United States Patent [19]
Lloyd et al.

[11] Patent Number: 6,080,106
[45] Date of Patent: Jun. 27, 2000

[54] PATIENT INTERFACE SYSTEM WITH A SCALE

[75] Inventors: Lester John Lloyd, Orinda; Melissa Ann Prince, San Francisco, both of Calif.

[73] Assignee: Alere Incorporated, San Francisco, Calif.

[21] Appl. No.: 08/958,689

[22] Filed: Oct. 28, 1997

[51] Int. Cl.[7] .................................................. A61B 5/00
[52] U.S. Cl. ......................... 600/300; 128/903; 128/904; 340/573; 340/666
[58] Field of Search .................................. 600/300, 301, 600/483, 513, 520; 128/903, 904; 340/500, 540, 573, 666; 200/666, 85 R, 86 R

[56] References Cited

U.S. PATENT DOCUMENTS

| | | |
|---|---|---|
| 3,791,375 | 2/1974 | Pfeiffer . |
| 3,890,958 | 6/1975 | Fister et al. . |
| 3,974,491 | 8/1976 | Sipe . |
| 4,383,533 | 5/1983 | Bhagat et al. . |
| 4,546,436 | 10/1985 | Schneider et al. . |
| 4,803,625 | 2/1989 | Fu et al. ................................. 600/300 |
| 4,838,275 | 6/1989 | Lee . |
| 5,007,429 | 4/1991 | Treatch et al. . |
| 5,012,411 | 4/1991 | Policastro et al. ....................... 600/301 |
| 5,019,974 | 5/1991 | Beckers . |
| 5,052,405 | 10/1991 | Batchelder . |
| 5,077,476 | 12/1991 | Rosenthal . |
| 5,182,707 | 1/1993 | Cooper et al. . |
| 5,241,965 | 9/1993 | Mick . |
| 5,276,432 | 1/1994 | Travis ..................................... 340/573 |
| 5,307,263 | 4/1994 | Brown . |
| 5,323,650 | 6/1994 | Fullen et al. . |
| 5,339,821 | 8/1994 | Fujimoto ................................. 600/300 |
| 5,385,069 | 1/1995 | Johnson, Jr. .............................. 73/571 |
| 5,544,649 | 8/1996 | David et al. ............................. 600/300 |
| 5,549,117 | 8/1996 | Tacklind et al. . |
| 5,584,297 | 12/1996 | Bodoet et al. . |
| 5,730,124 | 3/1998 | Yamauchi ................................ 600/300 |
| 5,810,747 | 9/1998 | Brundy et al. ........................... 600/300 |

OTHER PUBLICATIONS

Mridha et al., "Fluid Translocation Measurement," Scand j Rehab Med, vol. 21:63–69, 1989.

Capone, Robert et al., "The Effects of a Transtelephonic Surveillance and Prehospital Emergency Invervention System On The 1–year Course Following Acute Myocardial Infarction", American Heart Journal (1988) vol. 116, No. 4:1606–1615.

Chadda, Kul et al., "The Impact of Transtelephonic Documentation of Arrythmia on Morbidity and Mortality rate In Sudden Death Survivors," *American Heart Journal* (1986) vol. 112, No. 4: 1159–1165.

(List continued on next page.)

*Primary Examiner*—Linda Dvorak
*Assistant Examiner*—Bryan K. Yarnell
*Attorney, Agent, or Firm*—Karl Bozicevic Bozicevic, Field & Francis LLP

[57] ABSTRACT

A patient interface system for collecting and transferring data from a patient to a remote monitoring system, as well as methods for its use, are provided. The subject system uses: (a) a data collection device with a sensor and an interrogation device; (b) a processing device for processing the collected data; and (c) a communication device for transferring said collected data from the interface system to a remote monitoring system and receiving instructional data from a remote monitoring system. The subject system finds use in the remote monitoring of a variety of conditions, particularly in the remote monitoring of cardiac associated diseases. In addition, the sensor is a scale either programmed not to activate the patient interface system if it measures a weight below or above certain set weights or not to send measurements to the remote monitoring if it measures a weight below or above certain set weights.

17 Claims, 1 Drawing Sheet

OTHER PUBLICATIONS

Fleg, Jerome et al., "Physician Utilization of Laboratory Procedures to Monitor Outpatients With Congestive Heart Failure," *Arch. Intern. Med.* (1989) vol. 149:393–396.

Katz, Michael et al., "Detection of Preterm Labor by Ambulatory Monitoring of Uterine Activity: A Preliminary Report," *Journal of The American College of Obstetricians and Gynecologists* (1986) vol. 68, No. 4:773–778.

Patel, Umesh et al., "A Computer–Based, Automated, Telephonic System to Monitor Patient Progress in the Home Setting," *Journal of Medical Systems* (1992) vol. 16 No. 213:101–112.

Boland, R. et al., "Development and Evaluation of a Precision Forearm and Hand Volumeter and Measuring Cylinder," *J. Hand Ther* (1996) vol. 9, No. 4:349–358.

Breytenbach, H.S., "Objective Measurement of Post–Operative Swelling," *Int. J. Oral Surg.* (1978) vol. 7:386–392.

Dramaix, M. et al., "Serum Albumin Concentration, Arm Circumference, and Oedema and Subsequent Risk Of Dying In Children In Central Africa," *BMJ* (1993) vol. 307:710–713.

Kushner, Robert F., et al., "Estimation of Total Body water By Bioelectrical Impedance Analysis[1-3]," *The American journal of Clinical Nutrition* (1986) vol. 44:417–424.

Lindahl, O.A., et al., "Impression Technique for the Assessment of Oedema: Comparison With A New Tactile Sensor That Measures Physical Properties Of Tissue," *Med. & Biol. Eng. & Comput.*, (1995) vol. 33:27–32.

Miyazaki, S., et al., "Foot–Force Measuring Device For Clinical Assessment of Pathological Gait," *Med. & Biol. Eng. & Comput.* (1978) vol. 16:429–436.

Mridha, M. et al., "Fluid Translocation Measurement," *Scand j Rehab Med* (1989) vol. 21:63–69.

Mridha, M., et al., "Noninvasive Method For The Assessment of Subcutaneous Oedema," *Medical & Biological Engineering & Computing* (1986) vol. 24:393–398.

Davies et al., "An Automatic Device For The Measurement of Oedema In The Feet Of Rats and Guinea Pigs," *Med. & Biol. Enging.* (1971) vol. 9:567–570.

Starr, Thomas W., "A Computerized Device for the Volumetric Analysis of the Residual Limbs of Amputess," *Bulletin of Prosthetics Research BPR* 10–33 (1980) vol. 17, No. 1,:98–102.

Swedborg, Iwona, "Voluminmetric Estimation of the Degree of Lymphedema and its Therapy By Pneumatic Compression," *Scand J Rehab Med* (1977) vol. 9:131–135.

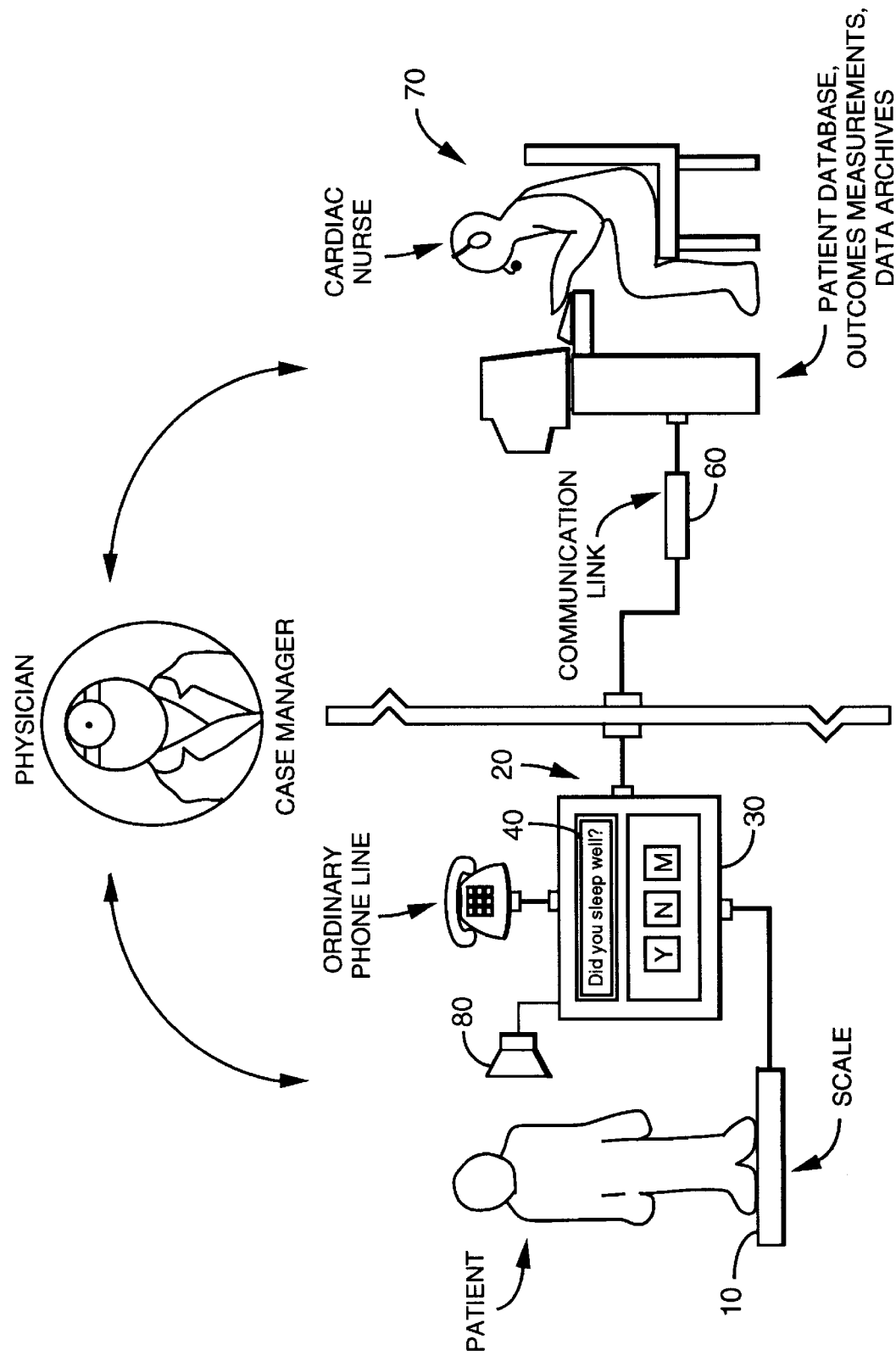

PATIENT INTERFACE SYSTEM WITH A SCALE

FIELD OF THE INVENTION

The field of this invention is patient monitoring systems.

BACKGROUND OF THE INVENTION

Frequent monitoring of patients permits the patients' physician to detect worsening symptoms as they begin to occur, rather than waiting until a critical condition has been reached. As such, home monitoring of patients with chronic conditions is becoming increasingly popular in the health care industry for the array of benefits it has the potential to provide. Potential benefits of home monitoring are numerous and include: better tracking and management of chronic disease conditions, earlier detection of changes in the patient condition, and reduction of overall health care expenses associated with long term disease management. The home monitoring of a number of diverse "chronic diseases" is of interest, where such diseases include diabetes, dietary disorders such as anorexia and obesity, respiratory diseases, AIDS and other chronic viral conditions, conditions associated with the long term use of immunosuppressants, e.g. in transplant patients, asthma, chronic hypertension, chronic use of anticoagulants, and the like.

Of particular interest in the home monitoring sector of the health care industry is the remote monitoring of patients with heart failure (HF), also known as congestive heart failure. HF is a syndrome in which the heart is unable to efficiently pump blood to the vital organs. Most instances of HF occur because of a decreased myocardial capacity to contract (systolic dysfunction). However, HF can also result when an increased pressure-stroke-volume load is imposed on the heart, such as when the heart is unable to expand sufficiently during diastole to accommodate the ventricular volume, causing an increased pressure load (diasystolic dysfunction). In either case, HF is characterized by diminished cardiac output and/or damming back of blood in the venous system. In HF, there is a shift in the cardiac function curve and an increase in blood volume caused in part by fluid retention by the kidneys. Indeed, many of the significant morphologic changes encountered in HF are distant from the heart and are produced by the hypoxic and congestive effects of the failing circulation upon other organs and tissues. One of the major symptoms of HF is edema, which has been defined as the excessive accumulation of interstitial fluid, either localized or generalized.

HF is the most common indication for hospitalization among adults over 65 years of age, and the rate of admission for this condition has increased progressively over the past two decades. It has been estimated that HF affects more than 3 million patients in the U.S. (J. B. O'Connell et al., J. Heart Lung Transpl. (1993) 13(4):S107–112).

In the conventional management of HF patents, where help is sought only in crisis, a cycle occurs where patients fail to recognize early symptoms and do not seek timely help from their care-givers, leading to emergency department admissions (Miller, P. Z., 1995, "Home monitoring for congestive heart failure patients," Caring Magazine, August 1995: 53–54). Recently, a prospective, randomized trial of 282 patients was conducted to assess the effect of the intervention on the rate of admission, quality of life, and cost of medical care. In this study, a nurse-directed, multi disciplinary intervention (which consisted of comprehensive education of the patient and family, diet, social-service consultation and planning, review of medications, and intensive assessment of patient condition and follow-up) resulted in fewer readmissions than the conventional treatment group and a concomitant overall decrease in the cost of care (M. W. Rich et al., New Engl. J. Med. (1995) 333:1190–95). Similarly, comprehensive discharge planning and a home follow-up program was shown to decrease the number of readmissions and total hospital charges in an elderly population (M. Naylor et al., Amer. College Physicians (1994) 120:999–1006).Therefore, home monitoring is of particular interest in the HF management segment of the health care industry.

Another area in which home-monitoring is of particular interest is in the remote monitoring of a patient parameter that provides information on the titration of a drug, particularly with drugs that have a consequential effect following administration, such as insulin, anticoagulants, ACE inhibitors, β-blockers, etc.

Although a number of different home monitoring systems have been developed, there is continued interest in the development of new monitoring systems. Of particular interest would be the development of a system that provides for improved patient compliance, ease of use, etc. Of more particular interest would be the development of such a system that is particularly suited for use in the remote monitoring of patients suffering from HF.

Relevant Literature

Monitoring systems are described in U.S. Pat. Nos. 5,241,965; 5,549,117; 5,584,297; 5,307,263; 4,803,625; 4,546,436; 5,007,429; 5,019,974; 5,077,476; 5,182,707; 4,838,275; as well as in Capone et al., Am. Heart J. (1988) 116: 1606; Chadda et al., Am. Heart J. (1986) 112: 1159; Fleg et al., Arch. Intern. Med. (1989) 149:393; Katz et al., Obstetrics & Gynecology (1986)68:773; Patel et al., J. Med. Sys. (1992) 16: 101.

Scientific American Medicine (Dale & Freeman eds) 1:II provides a review of heart failure, physical manifestations and methods for the treatment thereof.

Lindahl & Omata, Med. Biol. Eng. Comput. (1995) 33:27–32 provide a description of methods of assessing edema.

Other references of note include U.S. Pat. Nos.: 3,791,375; 3,890,958; 3,974,491; 4,144,749; 4,383,533; 5,052,405; 5,323,650; and 5,385,069; as well as Swedborg, Scand. J. Rehab. Med. (1977) 9:131–135; Mridha & Odman, Scand. J. Rehab. Med. (1989)21:63–39; Mridha & Ödman, Med. Biol. Eng. Comput. (1986) 24: 393–398; Kushner et al., Am. J. Clin. Nut. (1986) 44: 417–424; Breytenbach, Int. J. Oral Surg. (1978) 7:386–392; Davies et al., Med. Biol. Eng. Comput. (1971) 9:567–570; Lindhal et al., Med. Biol. Eng. Comput. (1991)29: 591–597; Iwakura, Med. Biol. Eng. Comput. (1978) 16:429–436; and Starr, BPR (1980) 17:98–102.

SUMMARY OF THE INVENTION

A patient interface system for collecting and transferring data from a patient to a remote monitoring system, and methods for its use in the management of a chronic condition, are provided. The subject interface system includes: (a) a patient data input means having both a sensor and a question and answer means; (b) a processing means; and (c) a communication means for transferring data to and from a remote monitoring means. Also provided is a patient monitoring system comprising the subject patient interface means operationally linked to the remote monitoring system. The subject patient interface system finds use in a variety of applications in which the condition of a patient is monitored remotely, and is particularly suited for use in the remote monitoring of patients suffering from a cardiac associated disease.

BRIEF DESCRIPTION OF THE FIGURES

FIG. 1 provides a schematic of the interface system of the subject invention and its use in the remote monitoring of a patient with a cardiac associated disease.

DESCRIPTION OF THE PREFERRED EMBODIMENTS

A patient interface system for collecting and transferring data from a patient to a remote monitoring system is provided. The subject system includes: (a) a patient data input means having both a sensor and a question and answer means; (b) a processing means; and (c) a communication means for transferring data to and from a remote monitoring system. Also provided is a patient monitoring system comprising the subject patient interface means operationally linked to the remote monitoring system. The subject patient interface system finds use in a variety of applications in which the condition of a patient is monitored remotely, and is particularly suited for use in the remote monitoring of patients suffering from a cardiac associated disease.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The subject patient interface system is suited for use in the collection and transfer of data from a patient having a condition to a remote monitoring system. The interface system of the invention may be used in the monitoring and management of a variety of different conditions, where such conditions include medically induced conditions, e.g. immunosuppression due to the chronic use of immunosuppressants as found in transplant patients, and naturally occurring disease conditions, such as diabetes, nutrition disorders, e.g. anorexia and obesity, AIDS and other virally associated conditions, asthma, chronic hypertension, chronic use of anticoagulants, and cardiac associated diseases, such as heart failure (HF), where the use of the subject interface system in the monitoring of patients with cardiac associated diseases is particularly preferred.

The first element of the subject interface system is the patient data input means that comprises both a sensor and an active interrogation means, i.e. a "question and answer" means. The sensor is capable of measuring a parameter diagnostic of the patient's health, i.e. a "diagnostic parameter. As used herein, a "sensor" is any device capable of measuring a physical characteristic or attribute of the patient, particularly a parameter diagnostic of the patient's health or condition. A parameter is "diagnostic" if it provides a physician with significant information about the patient's condition. For example, the degree of edema, weight, blood pressure, heart rate, temperature, and the like are all "diagnostic parameters" for some indications. It is preferred to employ a diagnostic parameter that correlates closely with the patient's condition, or any change in the patient's health. For example, HF patients may be monitored by following their degree of edema. Sensitive measurement of weight changes should correlate closely with edema, and may be used as a surrogate. Obese patients may be monitored by measuring their weight. Accordingly, the sensor may be any sensing means that is capable of measuring such parameters, such as a scale for measuring the patients weight, or a means for measuring the patient's blood pressure, oxygen saturation, ECG, blood glucose level, and the like. For systems designed for use in the monitoring of cardiac associated diseases, particularly HF, preferred are those embodiments of the subject invention in which the sensor is either: (1) a means for sensing edema, particularly edema of an extremity, such as: (a) the volume displacement measurement means as disclosed in U.S. patent application Ser. No.: 08/958,688 (Atty docket: ALE-2P); (b) the cross-sectional dimension measurement means as disclosed in U.S. patent application Ser. No. 08/959,342 (Atty docket: ALE-3P); (c) the pitting measurement means as disclosed in U.S. patent application Ser. No. 08/959,001 (Atty docket: ALE-4P); and the circumferential measurement means as disclosed in U.S. patent application Ser. No. 08/958,818 (Atty docket: JAN-1P), filed concurrently herewith, the disclosures of which are herein incorporated by reference; or (2) a weight detection means, such as a scale.

In addition to the sensor component, the data input means of the subject interface system also comprises an active interrogation means or "question and answer" means for presenting the patient with one or more questions related to the patients health status and recording the patient's answers to the questions. Questions which may be presented by the interrogation means may be simple "yes" or "no" questions, or be more complicated, requiring a more descriptive response or a selection of one of a plurality responses. The particular questions presented to the patient by the interface system will be chosen in view of the particular condition being monitored, or the state or progression of the condition being monitored, where representative questions include: (1) "Were you tired during the day?"; (2) "On a scale of 1 to 5, 5 being most, how tired were you in the middle of the day?"; (3) "Did you cough during the night?"; (4) "Did you need an extra pillow to sleep?"; (5) "Are your shoes tighter than usual?"; (6) "Did you exercise today?"; and the like. The questions may vary depending on the time of day in which they are asked, as certain questions may be more relevant in the morning than in the evening, etc. In addition to question, instructions information in the form of directions or suggestions may be given to the patient, e.g. (1) "Please take your blood pressure."; (2) "Don't forget to take your medicine."

The interrogation means may take any convenient form. For example, the question and answer means may be an input panel, where the input panel may be as simple as a toggle switch or pair of push buttons (e.g., "Yes/No"), or may comprise a full keyboard or touch-screen input system. Alternatively, the interrogation means may comprise a microphone, preferably coupled with voice-recognition software, where such software is known in the art. Audio answers may be recorded and transmitted unaltered, may be compressed, or may be "recognized", and transmitted in the form of a corresponding text file. The questions are drafted with the interrogation means in mind. For example, if the interrogation means comprises a series of five pushbuttons, the patient may be asked, for example, to rate his or her hunger or thirst on a scale of 1 to 5. If a keyboard is provided, the patient may type in any answer desired: this gives greater freedom to the patient but may make it more difficult to correlate and tabulate the patients records. Alternatively, keyboard answers may be restricted to a limited set (e.g., the patient may still be required to pick "choice a", "choice b", etc.). Since the patient may be partially incapacitated, it is preferred to simplify the interrogation means as much as possible, either by providing for spoken input or by limiting choices to a few push buttons.

The interrogation means may further provide information and/or questions to the patient, typically either visually or audibly. The questions may be displayed on a standard CRT, LED or LCD display, or played audibly over a speaker. One may also use a combination of these means for the first output means. For example, one may provide an LED display of the patient's weight, along with "spoken" questions. The system may also be provided with an additional "alarm tone" to remind the patient when readings should be taken. It is preferred to present questions either audibly, or typed on an easily-readable display. The questions may be provided in a number of different languages, with the appropriate language selected by either the patient or the monitoring staff.

In a preferred embodiment, the patient data input means will be automatic, by which is meant that the patient does not need to take any active steps to activate the patient data input means, e.g. the patient does not have to turn the means "on." For example, where the sensor is a scale, the patient need only step onto the scale. The input means will then sense the presence of the patient on the scale, determine and record the patient's weight, and automatically present to the patient one or more questions and record the patient's answers thereto.

The next component of the interface system is the processor means. The processor means may comprise any processor having sufficient power to store and present data, and may range from a microprocessor to a personal computer. The processor processes the data collected by the patient data input means in some manner. The processor means is capable of at least the following tasks: capturing data from the sensor; presenting a pre-selected series of questions to the patient, and capturing the patient's answers; and transmitting the data and patient answers to a remote monitoring system and/or monitoring staff, as described in greater detail below. Preferably, the processor is also capable of comparing the data captured from the sensor with a preset target value, e.g. comparing the captured data with preset minimum and maximum values; receiving instructional data from the remote monitoring system and effecting changes in the stored target value, minimum and maximum values, and question series presented to the patient in accordance therewith. Optionally, the processing means is further capable of presenting the captured data and any variation from the target value to the patient; detecting and verifying proper operation of the system (self diagnostics); and accepting and verifying a patient's id code or passcode, and employing the questions, target value, and minimum and maximum values appropriate to the identified patient. Preferably, the processing means includes no component which would allow a patient to self-analyze the collected data.

The next element of the subject interface system is the communication means, which serves to transmit data to, and receive data from, a remote monitoring system. As such, the communication means comprises both an output means for transferring the collected and processed data to a remote monitoring system and an input means for receiving instructional data from a remote monitoring system. The output and input means of the communication system may be combined as a single component or present as two separate components. The communication means will be any device or system capable of transmitting the data (measured parameters and patient answers) to the remote monitoring system, physician or staff, and receiving data (new target values, questions) from the remote monitoring system, e.g. for storage. Suitable communication means include modems, cable modems, LAN or WAN connections, radio/microwave and other wireless transmitter systems, and the like.

The input means will generally comprise a serial or parallel port to the processor means, but may alternatively or additionally comprise a keyboard or numeric pad, disc drive, and the like. In general, the input means is used by the physician or staff member to effect changes in the system's programming, for example altering the target value, changing the question series, or selecting an alternate question series or language. Alternatively, the input means may be identical with the interrogation means, e.g., the monitoring staff may use the patient's keyboard or keypad to enter changes, or may use the patient's microphone to enter voice commands or a verbal question series. In such cases, the system may be provided with a password, key, or voice recognition system to restrict access to the physician's programming mode" to the monitoring system and/or authorized staff. More preferably, however, the input means provides for remote entry of commands and data by the monitoring staff, and may be identical with the communication means, employing codes or passwords to distinguish authorized access from unauthorized access.

In using the subject interface system, the patient may activate the system by standing on the scale, by physically turning on the system, or by entering a passcode on the patient data input means, e.g. the input panel. If the patient's environment is relatively free of interference (for example, the patient does not live with small children or pets that are likely to activate the system by accident), it is preferred for the system to activate automatically once the patient stands on the scale. If more than one patient is to use the same system, it is preferred for each patient to have a separate ID code or passcode, used to activate the system. If desired, the code may be embedded in a magnetic card, so that the patient need only swipe the card through a reader, or press the card against a designated location on the system. Otherwise, the system may be provided with a simple "on/off" switch, preferably one which may shut off spontaneously after a predetermined period of inactivity.

The series of questions asked of the patient is preferably modified based on the patient's answers. For example, the patient may be asked if he or she ate a meal prior to being weighed. If the patient answers affirmatively, the patient may then be questioned about the size of the meal. If the patient answers negatively, he or she may be questioned about the length of time elapsed since the last meal (or the approximate time of the last meal). The patient may be asked if the correct medication was taken in a timely manner: if so, the processor proceeds on to the next topic; if not, the processor may begin a series of questions to determine why the medication was skipped (e.g., unpleasant side effects, advised by monitoring staff or staff member to discontinue, "just forgot," etc.).

The period of time which elapses between transmission of patient data from the subject interface system to the remote monitoring system will be one that is acceptable in view of the condition being monitored. For example, with cardiac associated diseases, an acceptable period of time may range from about 5 min to 1 week.

The subject invention will now be further described in terms of the figures. In one embodiment of the invention, as shown in FIG. 1, scale (10) provides a digital output to processor (20), which calculates the difference between the patient's weight and the preset target weight, and outputs the difference on display (40). The scale element (10) is suited for placement on the floor, while the remaining components are best placed on a desk or table. If the processor detects that the weight indicated by the scale is below a preset minimum weight (or above a preset maximum weight), the processor does not initiate the question sequence, and optionally displays a warning (e.g., "Unauthorized Use") on display (40). The processor then presents a series of predetermined questions to the patient through display (40) and/or speaker (80). The patient then responds by keying in answers on keyboard (30), while processor (20) records the answers. The keyboard has three buttons: Y=yes; N=no; and M=maybe (the buttons good represent different conditional gradations, such as "good," "better" and "worse," etc.). At the completion of the question series, processor (20) transmits the recorded answers through communications link (60) to the monitoring staff (70). The monitoring staff, upon examining the answers and data, may then alter the question series and/or download new questions, target values, and minimum and maximum values, consistent with his or her evaluation of the patient's health.

In operation, the patient steps onto scale portion, which automatically activates the processor. The processor compares the weight measured by scale portion with the minimum and maximum weights stored in memory. The minimum and maximum weights are set so that a person or animal much lighter or heavier than the patient will not activate the system inadvertently by stepping onto the scale. If the measured weight falls within the range defined by the minimum and maximum weights, the processor compares the measured weight with the patient's target weight, as established by the patient's physician. The measured weight and deviation (if any) from the target weight is displayed on visual display, and is stored for later transmission to the monitoring staff. The system may also display a greeting, such as by visually displaying "Good morning <patients name>". Preferably, the system also issues a "spoken" greeting through a speaker, e.g., "Good morning, <patient's name>, are you ready to begin?" The system then presents the predetermined questions selected by the patient's physician, designed to elicit the state of the patient's condition. The patient responds by pressing the button that corresponds to the desired answer, or, optionally, the patient simply speaks his or her responses into microphone. The processor records the answers, whether from button or microphone. Once the series of questions and answers is completed, the processor optionally informs the patient that the questions are completed (visually and/or aurally), and transmits the measured data and patient's answers to the monitoring staff via modem (contained within a base). While connected to the monitoring staff s computer, the answers and data are examined by the monitoring staff (or compared immediately by the monitoring staff's computer), and new questions, target value, and minimum/maximum values are downloaded to the processor. For example, if the patient's responses indicate developing intolerance to the medication prescribed, the new set of questions may include questions designed to identify the symptoms and severity of the intolerance, so that the physician can tell if the patient adjusts to the medication, or if a different medication will need to be substituted.

As discussed above, the subject interface system is useful in the remote monitoring of a diverse number of different patient conditions. For example, the subject interface system finds use in the monitoring of drug titration where a physiological parameter can be measured and related to the effect of a drug that is being self-administered, e.g. insulin, anticoagulants, ACE inhibitors, β-blockers, and the like. Of particular interest is the use of the subject invention in the remote monitoring of cardiac associated diseases, such as HF, where of particular interest is the embodiment of the subject invention comprising a means for measuring edema of a patient extremity as the sensor.

Also provided is a complete remote monitoring system which includes both the subject patient interface system in operational combination with a remote monitoring means or device. A number of different remote monitoring devices are known in the art and may be operationally linked with the subject patient interface system, as described in U.S. Pat. Nos.: 5,601,435; 4,418,700; 4,566,461; and the like, the disclosures of which are herein incorporated by reference.

It is evident from the above discussion that the subject invention makes a significant contribution to the field of chronic condition management. The patient interface system described herein permits the physician to conduct such monitoring economically and rapidly, as it does not require either the physician, nurse or the patient to travel. This interface system both measures physical data and interrogates the patient through a series of simple questions designed to elicit any important changes or factors in the patient's health. Such questions can be used to obtain information that cannot otherwise be practically obtained without very intrusive or expensive monitoring. The subject interface system is also easy to use and should therefor result in better patient compliance and a concomitant increase in the reliability of the data collected and the effectiveness of the treatment regimen provided to the patient.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A patient interface system for use in collecting and transferring data from a patient to a remote monitoring system, said system comprising:
   (a) a patient data input and data receiving means comprising:
      (i) a sensor comprising a scale programmed not to activate the patient interface system if it measures a weight below or above certain set weights; and
      (ii) an interrogation means comprising a means for creating visual and audio signals;
   (b) a processing means capable of receiving and storing data from said patient data input means;
   (c) a communication means capable of transferring said processed patient data from said processing means to a remote monitoring system and receiving instructional data from said remote monitoring system.

2. The system according to claim 1, wherein said processing means is further capable of storing a predetermined target value and a series of questions.

3. The system according to claim 2, wherein said processing means is further capable of comparing a sensor measured physiological parameter with said predetermined target value to determine a variance.

4. The system according to claim 2, wherein said processing means is capable of accepting and storing a new predetermined target value and series of questions from said remote monitoring system.

5. The system according to claim 1, wherein said sensor further comprises an edema sensor means for measuring edema of an extremity.

6. The system according to claim 1, wherein said interrogation means further comprises at least one of a keyboard, a plurality of buttons and a microphone.

7. The system according to claim 1, wherein said communication means comprises at least one of a modem, a serial interface, a LAN connection and a wireless transmitter.

8. A patient interface system for use in collecting and transferring data from a patient suffering from a cardiac associated disease to a remote monitoring system, said system comprising:
   (a) a patient data input and data receiving means comprising:
      (i) a sensor means comprising a scale programmed not to activate the patient interface system if it measures a weight below or above certain set weights; and
      (ii) an interrogation means comprising a means for creating visual and audio signals;
   (b) a processing means capable of:
      (i) receiving and storing data from said patient data input means;
      (ii) storing a predetermined target value and a series of questions;
      (iii) comparing said sensor measured diagnostic parameter with said predetermined target value to determine a variance; and
      (iv) accepting and storing a new predetermined target value and series of questions from said remote monitoring system; and
   (c) a communication means capable of transferring said patient data from said processing means to a remote monitoring system and receiving instructional data from said remote monitoring system.

9. The system according to claim 8, wherein said interrogation means further comprises at least one of a keyboard, a plurality of buttons and a microphone.

10. The system according to claim 8, wherein said communication means comprises at least one of a modem, a serial interface, a LAN connection and a wireless transmitter.

11. The system according to claim 8, wherein said sensor means further comprising an edema sensor means for measuring edema by measuring volume displacement.

12. The system according to claim 8, wherein said sensor means further comprising an edema sensor means for measuring edema by measuring a cross-sectional dimension.

13. The system according to claim 8, wherein said sensor means further comprising an edema sensor means for measuring edema by measuring pitting.

14. A method for collecting and transferring data from a patient having a condition to a remote monitoring system, said method comprising:
   (a) obtaining a weight measurement with a scale programmed not to send measurements to the remote monitoring system if it measures a weight below or above certain set weights;
   (b) processing said weight measurement with a processing means; and
   (c) transferring said processed weight measurement with a communication means to the remote monitoring system.

15. The method according to claim 14, wherein said processing comprises comparing said weight measurement with a predetermined target value to determine a variance, wherein said processing means stores said predetermined target value and a series of questions.

16. The method according to claim 15, wherein said method further comprises changing at least one of said predetermined target value and series of questions in response to said data.

17. The method according to claim 14, wherein said condition is a cardiac associated disease.

\* \* \* \* \*